United States Patent [19]

Chipens et al.

[11] 4,187,217
[45] Feb. 5, 1980

[54] BRADYKININ CYCLIC ANALOG-CYCLO-[(N$^\epsilon$-1-L-LYSINE, 6-GLYCINE)-BRADYKININ]

[76] Inventors: Gunar I. Chipens, ulitsa Lenina, 84, kv. 5; Felix K. Mutulis, ulitsa Bikrnieku, 77, kv. 52; Inta P. Misinya, ulitsa St. Mangali, 7, kv. 1, all of Riga, U.S.S.R.

[21] Appl. No.: 967,609

[22] Filed: Dec. 8, 1978

[30] Foreign Application Priority Data

Dec. 14, 1977 [SU] U.S.S.R. .............................. 2555261

[51] Int. Cl.$^2$ ...................... C07C 103/52; C07G 7/00
[52] U.S. Cl. ................................ 260/112.5 R; 424/177
[58] Field of Search ................................ 260/112.5 R

[56] References Cited

U.S. PATENT DOCUMENTS

| | | | |
|---|---|---|---|
| 3,216,991 | 11/1965 | Ondetti et al. | 260/112.5 R |
| 3,216,993 | 11/1965 | Bodanszky et al. | 260/112.5 R |
| 3,256,267 | 6/1966 | Boissonnas et al. | 260/112.5 R |

Primary Examiner—Delbert R. Phillips
Assistant Examiner—Blondel Hazel
Attorney, Agent, or Firm—Lackenback, Lilling & Siegel

[57] ABSTRACT

Cyclic analog of bradykinin having the formula

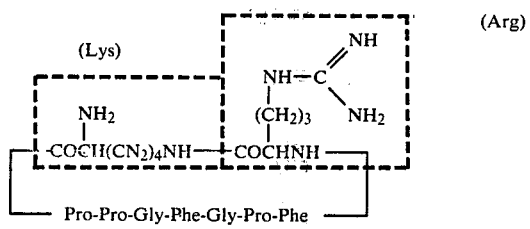

where Lys-L-lysine residue, Pro-L-proline residue, Gly-glycine residue, Phe-L-phenylalanine residue, Arg-L-arginine residue. The present compound can create prolonged depressor effect in experiments in vivo, as well as increase vascular permeability in experiment in situ less than bradykinin. In experiments in vitro this compound displays no myotropic effect.

1 Claim, No Drawings

BRADYKININ CYCLIC ANALOG-CYCLO-[(N$^\epsilon$-1-L-LYSINE, 6-GLYCINE)-BRADYKININ]

This invention relates to novel synthetic analogs of known natural tissue hormone of bradykinin.

FIELD OF APPLICATION

Bradykinin and other peptides containing amino-acid sequence of bradykinin, e.g. callidin, methionyl lysyl bradykinin, kinins of animal and insect poisons, are widely abundant in nature and fulfill important functions of regulating biochemical and physiological processes in animals and humans. Various diseases and pathological conditions of human organisms are connected with disturbances in the dynamics of formation and decomposition of bradykinin and related peptides. Therefore, there is an urgent need in bradykinin analogs and antimetabolites possessing ability to affect and modify these processes (T. S. Paskhina. Biochemical principles of pathology of cardiovascular system. In: "Molecular principles of pathology", M., "Medicina", 1966, pp. 123–178; A. A. Dzizinsky, O. A. Gomazkov. "Kinins in physiology and pathology of cardiovascular system", Novosibirsk, 1976 (In Russian).

BACKGROUND OF INVENTION

Natural bradykinin itself is of no use for these purposes. Its main drawback is short duration of effect (bradykinin half-life period in human blood is 30 sec) (K. A. Saameli, T. K. Eskes. Am. J. Physiol., 203,261 (1962) and a wide spectrum of biologic effects, i.e., absence of selectivity. So, the hormone affects smooth muscles, circulatory system, permeability of capillary vessels and exerts many other effects (E. Schroeder, C. Luebke. "Peptides", vol. 2, M., "Mir", 1969, pp. 112–117 (In Russian)). Therefore, therapeutic application of bradykinin can result in intolerable side effects. The same can be said about bradykinin synthetic analogs which account for more than 170 (Handbook of Experimental Pharmacology, vol. XXV. Bradykinin, Kallidin and Kallikrein. Ed. E. G. Erdos. Springer-Verlag, Berlin-Heidelberg, New York, 1970, pp. 1–768). No compounds were found among them which possess marked selectivity and prolongation of biologic effect.

OBJECT OF INVENTION

The object of the present invention consists in the synthesis of the novel bradykinin analog possessing marked selectivity and prolongation of biologic effect.

BRIEF DESCRIPTION OF INVENTION

According to the invention there is proposed bradykinin cyclic analog—cyclo-(N $\epsilon$-1-L-lysine, 6-glycine)-bradykinin(BCA)

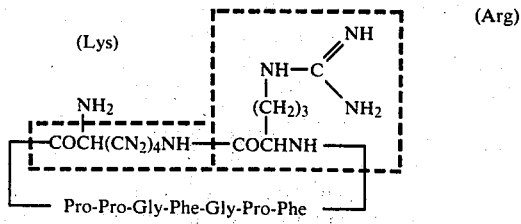

where Lys—L-lysine residue, Pro—proline residue, Gly—glycine residue, Phe—L-phenylalanine residue,
Ard—L-arginine residue. The present compound can create prolonged depressor effect in experiments in vivo, as well as increase vascular permeability in experiment in situ less than bradykinin. In experiments in vitro this compound displays no myotropic effect.

This compound possesses exclusive selectivity of action with a sharply prolonged half-life period, i.e. valuable properties from the point of view of therapeutic application.

In the test for decrease in rat blood pressure (dose 50 µg/kg) BCA exhibits activity approximately equal to that of bradykinin, though, if the bradykinin effect completely disappears 1.5 min after the hormone administration, then BCA at its single administration yields stable decrease in blood pressure for 3 hrs. At the same time, BCA displays no myotropic activity which is so characteristic for kinins (test for contraction of rat ileum), i.e., it has pronounced selectivity of action.

The compound proposed of the above formula is obtained by the method which, according to the invention, includes the following stages.

(a) benzyloxycarbonylproline is reacted with tert-butyl ester of glycine to obtain tert-butyl ester of benzyloxycarbonylprolyglycine;

(b) the product of stage (a) is hydrogenated to obtain tert-butyl ester of prolyglycine;

(c) tert-butoxycarbonylnitroarginine is reacted with p-nitrophenyl ester of α-benzyloxycarbonyllysine to obtain p-nitrophenyl ester of α-benzyloxycarbonyl, $\epsilon$-tert-butoxycarbonylnitroarginyllysine;

(d) the product of stage (c) is reacted with proline to obtain α-benzyloxycarbonyl, $\epsilon$-(tert-butoxycarbonylnitroarginyl)lysylproline;

(e) the product of stage (d) is treated with trifluoroacetic acid to obtain trifluoroacetate of α-benzyloxycarbonyl, $\epsilon$-(nitroarginyl) lysylproline;

(f) p-nitrophenyl ester of tert-butoxycarbonylphenylalanine is reacted with glycine to obtain tert-butoxycarbonylphenylalanylglycine;

(g) the product of stage (f) is reacted with p-nitrobenzyl ester of prolylphenylalanine to obtain tert-butoxycarbonylphenylalanylglycylprolylphenylalanine p-nitrobenzylester;

(h) the product of stage (g) is treated with hydrazine hydrate to obtain hydrazide of tert-butoxycarbonylphenylalanylglycylprolylphenylalanine;

(i) the products of stages (e) and (h) are reacted to obtain α-benzyloxycarbonyl, $\epsilon$-(tert-butoxycarbonylphenylalanylglycylprolylphenylalanylnitroarginyl)-lysylproline;

(j) the products of stages (b) and (i) are reacted to obtain tertbutyl ester of α-benzyloxycarbonyl, $\epsilon$-(tert-butoxycarbonylphenylalanylglycylprolylphenylalanylnitroarginyl)lysylprolylglycine;

(k) the product of stage (j) is transformed into hydrochloride of α-benzyloxycarbonyl, $\epsilon$-(phenylalanylglycylprolylphenylalanylnitroarginyl)lysylprolylglycine;

(l) the product of stage (k) is cyclized to obtain cyclo-[α-benzyloxycarbonyl, $\epsilon$-(phenylalanylglycylprolylphenylalanylnitroarginyl)lysylprolylprolylglycyl];

(m) the product of stage (l) is hydrogenated to obtain cyclo-[(N$^\epsilon$-1-L-lysine, 6-glycine)-bradykinin].

DETAILED DESCRIPTION OF INVENTION

For better understanding of the invention hereinbelow an Example is given of the compound preparation with synthesis scheme enclosed, as well as the results of biologic tests.

All amino acids, except glycine, have L-configuration. Melting points which were determined in open capillaries are given without correction. Individual compounds obtained were examined by TLC on plates "Silufol" UV 254 in systems:A - chloroform-ethanol-ethyl acetate-acetic acid-water (85:5:8:2:0.25); B - chloroform-ethanol-n-butanol-ethyl acetate-water (10:6:4:3:1); C—chloroform-methanol-water (40:30:5); D—butanol-acetic acid-water (4:1:1); E—ethyl acetate-pyridine-acetic acid-water (5:5:1:3), as well as by electrophoresis on paper Fn 16 in 1 N or 5 N acetic acid. Electrophoretic mobility $E_{His}$ was determined with respect to histidine. Spots of substances were detected by examination of chromatograms in UV rays, as well as by spraying with ninhydrin or with chlorine - benzidine reagent. For all the compounds the data of elementary analysis satisfactorily coincided with calculated content of C,N,H. To identify compounds PMR at 60 mHz was used. Chemical shifts, form and intensity of signals corresponded to expected structures. Amino-acid analysis was carried out after peptide hydrolysis in soldered ampule at 110° for 24 hrs.

(a) Tert-butyl ester of benzyloxycarbonylprolylglycine (E 8-9). 10.0 g (40 mmol) of benzyloxycarbonylproline are dissolved in 50 ml of dimethylformamide, 4.45 ml (40 mmol) of N-methylmorpholine, as well as cooled solution of 5.30 ml (40 mmol) of isobutyl chlorocarbonate in 10 ml of dimethylformamide are added by drops at −15°. Then the reaction mixture is stirred for 30 min at −15° C., and cooled suspension of 10.6 g (50 mmol) of phosphite of glycine tert-butyl ester in 100 ml of dimethylformamide and 0.56 ml (50 mmol) of N-methylmorpholine are added. The mixture is stirred for 15 hrs at −15°, then the reaction vessel is kept for 15 hrs at −10° C. Solvent is vacuum-evaporated, the residue is dissolved in the mixture of 100 ml of ethyl acetate and 100 ml of water, ethyl acetate layer is washed with 10% solution of potassium bicarbonate and potassium bisulphate with water, dried with magnesium sulphate, filtered and evaporated. The oil obtained is crystallized by treatment with mixture of ether with hexane (1:1). Yield: 9.2 g (63%). M.p. 71°–72° C.; $[\alpha]_D^{20} = -49.0°(c=2$, dimethylformamide). $R_f=0.55$ (A); 0.64 (B); 0.68 (C).

(b) Tert-butyl ester of prolylglycine (F 8-9). 5.0 g (13.8 mmol) E 8-9 are hydrated in the solution of 50 ml of ethanol in the presence of palladium black for 5 hrs. After the catalyst was filtered off, solvent is evaporated, the residue is dissolved in the mixture of dry ester with hexane (1:2) and reevaporated, crystallization taking place. Colorless crystalline substance is obtained after complete evaporation. Yield 2.8 g (89%). M.p. 56°–57° C.; $[\alpha]_D^{20} = -38.6°(c=1$, dimethylformamide). $E_{His}=0.83$ (1 N acetic acid). $R_f=0.28$ (C); 0.15 (D); 0.70 (E).

(c) P-nitrophenyl ester of α-benzyloxycarbonyl-ε-(tert-butoxycarbonyl) nitroarginyl-lysine(C 5-6). 4.63 ml (34.3 mmol) of isobutyl chlorocarbonate are added to the solution of 12.8 g (34.3 mmol) of tert-butyloxycarbonylnitroarginine and 3.80 ml (34.3 mmol) of N-methylmorpholine in 100 ml of dimethylformamide at −15° C. Then 10.0 g (22.8 mmol) of powder of chlorohydrate of p-nitrophenyl ester of α-benzyloxycarbonyllysine are added. The mixture is stirred for 30 min at −10° C., then a solution of 2.55 ml (22.8 mmol) of N-methylmorpholine in 50 ml of dimethylformamide is added drop by drop for 2 hrs. After stirring for 30 min at −20° C., 1.33 ml (12.1 mmol) of β-dimethylaminoethylamine are added. After stirring for 30 min the solvent is evaporated, the residue is dissolved in the mixture of 100 ml of ethyl acetate and 100 ml of water. The ethyl acetate layer is washed with 10% solutions of potassium bicarbonate and potassium bisulphate (twice) and water. The layer is dried with magnesium sulphate, filtered off and evaporated. Yellowish amorphous substance is obtained. Yield 13.5 g (85.5%). $R_f=0.80$ (A); 0.90 (D). $[\alpha]_D^{20} = -20.9°(c=1$, dimethylformamide).

(d) α-Benzyloxycarbonyl-ε-(tert-butyloxycarbonylnitroarginyl)lysylproline (D 5-7). 10.0 g (14.2 mmol) C 5-6 are dissolved in 100 ml of dimethylformamide, 2.46 g (21.4 mmol) of fine triturated proline and 1.66 ml (1.49 mmol) of N-methylmorpholine are added and stirred on a magnetic stirrer for 20 hrs. Then the solvent is evaporated, the residue is dissolved in the mixture of 100 ml of ethyl acetate and 100 ml of 10% potassium bisulphate solution, the water layer being separated, and ethyl acetate layer extracted with 10% potassium bisulphate solution and then with 10% potassium bicarbonate solution. Water-bicarbonate layer is separated, neutralized with excess of 10% potassium bisulphate solution to pH 2 and extracted with ethyl acetate (2×100 ml). The extract is dried with magnesium sulphate, filtered off and evaporated. Colorless amorphous substance is obtained.

Yield 7.9 g (82.0%). $[\alpha]_D^{20}=23.1°(c=1$, dimethylformamide). $R_f=0.54$ (A); 0.81 (D).

(e) Trifluoroacetate of α-benzyloxycarbonyl-ε-(nitroarginyl)lysylproline. (E 5-7). 5.0 g (7.37 mmol) D 5-7 are dissolved in the mixture of trifluoroacetic acid and methylene chloride (1:1) at cooling to 0° C., then kept for 20 min at room temperature, then evaporated at room temperature until dry. The residue is triturated with dry ether, the resulting solid substance is filtered off and washed with dry ether on the filter. The yield of colorless amorphous substance 5.0 g (98%). $E_{His}=0.49$ (5 N acetic acid), $[\alpha]_D^{20}=11.1°(c=1$, dimethylformamide). $R_f=0.57$ (C); 0.70 (E).

(f) Tert-butoxycarbonylphenylalanylglycine (C 1-2). 6.4 g (16.6 mmol) p-nitrophenyl ester of tert-butoxycarbonylphenylalanine, 1.13 g (15 mmol) glycine and 1.67 ml (15 mmol) N-methylmorpholine are dissolved in the mixture of 200 ml dimethylformamide and 20 ml water. The solution is kept for 20 hrs at room temperature, evaporated and the remaining oil is dissolved in a mixture of 80 ml 10% aqueous solution of potassium bicarbonate and 50 ml ethylacetate. Ethyl acetate layer is separated and aqueous layer is extracted with ether (50 ml) and neutralized with excess of 10% aqueous solution of potassium bisulphate (to pH 2). The obtained solution is extracted with ethyl acetate, (2×50 ml), the extract is washed with water (50 ml) and dried on anhydrous magnesium sulphate, filtered and evaporated until dry. A colorless crystalline substance is obtained. The yield 4.0 g (82.7%). For analytical purposes the substance is crystallized from ethyl acetate. Melting point 165° with decomp. $[\alpha]_D^{20} = -9.0°(c=1$, dimethylformamide). $R_f=0.85$ (A), 0.90 (B), 0.88 (C).

(g) p-Nitrobenzyl ester of tert-butoxycarbonylphenylalanylglycylprolyl-phenylalanine (D 1-4), 2,80 g (8.7 mmol) C 1-2 are dissolved in 50 ml of dry dimethylformamide, added 1.84 g (10 mmol) pentafluorophenol, cooled to −20° and introduced 1.90 g (9.2 mmol) dicyclohexylcarbodimide, then shaken until the latter is dissolved and kept for 30 min at 0°. Then 4.15 g (8.7 mmol) hydrobromide of p-nitrobenzyl ester of prolylphenylalanine (C 3-4) (A. P. Pavars, G. I. Chipens. "Zh. Obshch. Khim.", 41, 459(1971), and 0.97 ml (8.7 mmol) of N-methylmorpholine are added. The mixture is kept at room temperature, pH of the medium being controlled (a drop of solution is placed on damp indicator paper); N-methylmorpholine is added dropwise in the course of the reaction to maintain pH 8. Three hrs after the introduction of amino component, the mixture is evaporated, to the residue is added 100 ml methylene chloride, filtered. The filtrate is washed subsequently with 10% solutions of potassium bicarbonate, potassium bisulphate and water, then dried on anhydrous magnesium sulphate, filtered and evaporated. The obtained oil is crystallized by triturating with dry ether. The yield 5.4 g (88.4%). Melting point 125°–155°. $[\alpha]_D^{20} = -45.6°$ (c=1, dimethylformamide). $R_f = 0.88$ (A), 0.91 (B), 0.91 (D).

(h) Hydrazide of tert-butoxycarbonylphenylalanineglycylprolylphenylalanine (E 1-4). 3.0 g (4.26 mmol) D 1-4 and 1.0 ml of hydrazine hydrate are heated for 1 hr in 30 ml ethanol at 70°, then filtered; to the filtrate is added 50 ml water and kept for 20 hrs at −10°, filtered off and crystals on the filter are washed with 30 ml 50% aqueous ethanol, then with water until the neutral reaction of the filtrate. Dried on $P_2O_5$. The yield 2.30 g (92.8%). Melting point 140°–160°. $[\alpha]_D^{20} = -59.8°$ (c=1, dimethylformamide). $R_f = 0.93$ (A); 0.92 (B); 0.91 (D).

(i) α-benzyloxycarbonyl-ε-(tert-butoxycarbonylphenylalanylglycylprolylphenylalanylnitroarginyl)lysylproline (F 1-7). 2.1 g (3.62 mmol) E 1-4 are dissolved in 50 ml dimethylformamide, cooled to −30° and with stirring is added a cooled (−70°) mixture of 3.5 ml (15.7 mmol) 4.5 N solution of dry hydrogen chloride in tetrahydrofuran and 20 ml ethyl acetate. Then a cooled solution of 0.45 ml (3.87 mmol) tert-butylnitrite in 10 ml ethyl acetate is added dropwise at −30°. The mixture is kept for 30 min at −25°, then 1.76 ml (15.8 mmol) N-methylmorpholine are added and solution of 2.68 g (3.87 mmol) E 5-7 and 0.44 ml N-methylmorpholine in 50 ml dimethylformamide. The mixture is kept for 3 days at −10°, evaporated, the residue is dissolved in a mixture of 100 ml methylene chloride and 100 ml water. The layer of methylene chloride is separated, washed subsequently with 10% solutions of potassium bicarbonate, potassium bisulphate and water (by 100 ml), dried on anhydrous magnesium sulphate, filtered and evaporated. The obtained oil is crystallized by triturating with a mixture of ether and ethyl acetate (1:1). The yield 3.50 g (85.8%). Melting point 140°–177°. $[\alpha]_D^{20} = -44.1°$ (c=1, dimethylformamide). $R_f = 0.53$ (A); 0.84 (B); 0.87 (D).

(j) Tert-butyl ester of α-benzyloxycarbonyl-ε-(tert-butoxycarbonylphenylalanylglycylptolylphenylalanylnitroarginyl)lysylprolylprolylglycine(G 1-9). 2.70 g (2.40 mmol) F 1-7 are dissolved in 40 ml dimethylformamide, cooled to 0° and added 2.19 g (2.89 mmol) of dicyclohexylcarbodiimide - pentafluorophenol complex ("complex F") (J. Kovacs, L. Kisfaludy, M. Q. Ceprini., J. Am. Chem. Soc., 89, 183, (1967), and 1.1 g (4.8 mmol) tert-butyl ester of prolylglycine (F 8-9). The mixture is kept for 20 hrs at room temperature, evaporated, the residue is dissolved in 50 ml methylene chloride, filtered, the filtrate is washed with 50 ml 10% solution of potassium bisulphate and 50 ml water. Dried on anhydrous magnesium sulphate, filtered, evaporated. The residue is twice dissolved in minimum volume of methylene chloride and precipitated with ether. The yield 2.8 g (87.2%). Melting point 150°–193° with decomp. $[\alpha]_D^{20} = -60.3°$ (c=1, dimethylformamide). $R_f = 0.57$ (A); 0.68 (B); 0.60 (D).

(k) Hydrochloride of α-benzyloxycarbonyl-ε-phenylalanylglycylprolylphenylalanylnitroarginyl)lysylprolylprolylglycine (H 1-9). 1.8 g (1.346 mmol) G 1-9 are dissolved at 0° in 20 ml of the mixture of trifluoroacetic acid and methylene chloride (1:1), kept for 20 min at room temperature and evaporated at 0°. The residue is crystallized by triturating with 50 ml dry ether, dissolved in 10 ml dry dimethylformamide, added 0.33 ml (1.5 mmol) 4.5 N solution of anhydrous hydrogen chloride in tetrahydrofuran and precipitated with 100 ml dry ether. The yield 1.55 g (95%). $[\alpha]_D^{20} = -77.8°$. Melting point 140°–192°. $R_f = 0.73$ (C); 0.74 (E).

(l) Cyclo-[α-benzyloxycarbonyl- ε-(phenylalanylglycylprolyl-phenylalanylnitroarginyl)lysylprolyl-prolylglycyl](I 1-9). 1.1 g (0.91 mmol) H 1-9 are dissolved in 2 1 dimethylformamide (dried on barium oxide and distilled on ninhydride immediately before use) and at stirring in an atmosphere of dry argon at 0° 1.5 g (1.98 mmol) of dicyclohexycarbodiimidepentafluorophenol complex (1:3) ("complex F") are added (J. Kovacs, L. Kisfaludy, M. Q. Ceprini. J. Am. Chem. Soc., 89, 183 (1967). Then at stirring in argon atmosphere at room temperature 0.19 ml (1.38 mmol) of triethylamine dissolved in 300 ml dimethylformamide are added during 6 hrs. The obtained mixture is kept at room temperature for 2 days and evaporated at 28°. The oil residue is crystallized by triturating with dry ether, filtered, the residue on the filter is washed with ether, then with water. The obtained product is subjected to TLC in system B. It is assumed that substance with $R_f = 0.6$ is the required cyclopeptide (one of the main cyclization products, chromatographically mobile, is detected by UV light and benzidine reagent). Cyclization mixture is preliminarily purified on a column (2 ×100 cm) with silica gel (average particle size 20μ, obtained by fractioning of 5/40μsilicagel, "Chemapol", Czechoslovakia). Chloroform-ethanol-n, butanol-ethyl acetate (10:6:4:3) system being used as eluent, dicyclohexyurea and a number of substances of peptide nature are separated. Fractions containing the presumed cyclopeptide are purified once more on a column with silicagel (3×250 cm, average particle size 20μ) using system B as eluent, collecting fractions by 20 ml and registering absorption at 280 nm ("Uvicord II"). Fractions 55 to 66 are evaporated, the residue is treated with ether. 102 mg (9.73%) of crystalline substance are obtained. Melting point 163°–165°. Chromatographically pure (tested by TLC on "Merck" plates in 6 systems). $R_f = 0.47$ (B). Mol. weight: found 1024 (determined cryoscopically, using urea melting) (A. Ya. Berlin. "Laboratory technique in organic chemistry". M., Goskhimizdat, 1963, 348 (In Russian), calculated 1163.313 $[\alpha]_D^{20} = -64.1$ (c=0.5, dimethylformamide). $R_f = 0.37$ (A), 0.43 (B), 0.89 (C), 0.37 (D), 0.96 (E).

(m) Cyclo-[(ε-phenylalanylglycylprolyl-phenylalanylarginyl)lysylprolylprolylglycyl] diacetate (cyclo-[(N$^\epsilon$-1-L-lysine-6-glycine) bradykinin], J 1-9). 50 mg (0.043 mmol) I 1-9 are dissolved in 5 ml acetic acid and hydrated for 20 hrs in the presence of palladium black. Then the catalyst is filtered off and the filtrate is lyophilized. The residue is lyophilized from 10 ml water, then once more dissolved in 10 ml water, filtered through a membrane filter "Synpore" and lyophilized.

White friable powder is obtained. Chromatographically homogeneous. $[\alpha]_D^{20} = -76°$ (c=0.65, H$_2$O). The yield 45.7 mg (96%). $R_{His}=0.65$ (1 N acetic acid). $R_f=0.69$ (E). Amino-acid analysis: proline 2.83, glycine 1.90, phenylalanine 1.93, lysine 1.00, arginine 1.23. At tryptic splitting (T. Devenai, Ya. Gergei. "Amino acids, peptides, proteins". M., "Mir", 1976, 168 (In Russian)) of the drug only one substance is formed (E$_{His}$=0.82 1 N acetic acid) which testifies to the cyclic structure of the peptide.

Testing of cyclo-[(N$^\epsilon$-1-L-lysine-6-glycine)bradykinin] for decrease in blood pressure in anaesthesized rats showed that bradykinin cyclic analog (BCA) unlike bradykinin (BK) possesses marked prolonged effect. Threshold concentration of BCA is 5 μg/kg (0.5 μg/kg for BK). At a concentration of 50 μg/kg BCA has equipressor effect as compared to BK, but it is prolonged considerably. In the case of BCA blood pressure remains reduced by 30-40 mm for 1-2 hrs with subsequent recovery of 40-50% of the initial level (2-3 hrs following the beginning of administration).

It has been established in experiments in vitro (J. M. van Rossum. Arch. Int. Pharmacodyn., 143, 299 (1963)) on isolated rat uterus and ileum that within $10^{-10} - 10^{-5}$ mol/l concentrations BCA lacks myotropic effect characteristic of natural bradykinin. At these concentrations BCA doe not affect BK myotropic activity, Effect of increase in vascular permeability (N. Isokane. The Ochanomizu Med. J., 13, 362 (1965)) is lower in BCA than in BK; reactions are comparable at concentrations of 1 mg/kg and 25 μg/kg, respectively.

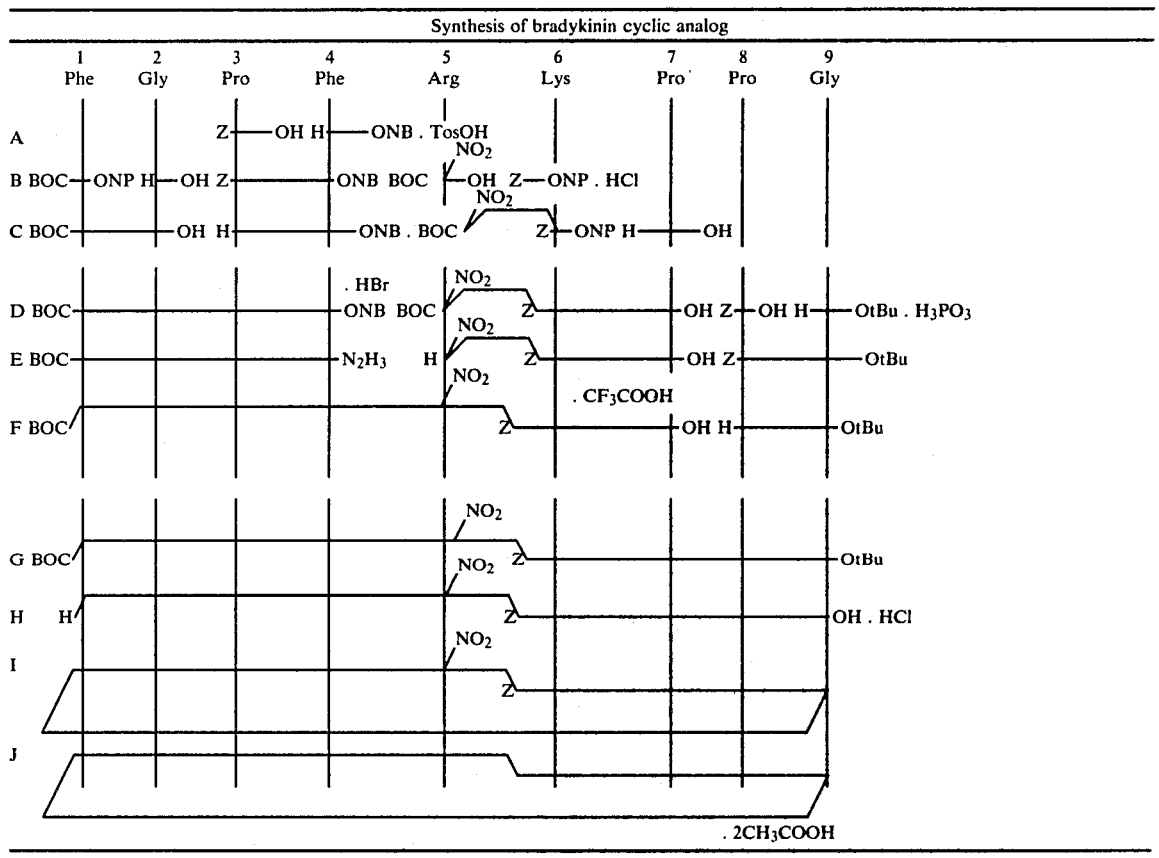

Synthesis of bradykinin cyclic analog

What is claimed is:

1. Cyclic analog of bradykinin - cyclo[(N-$^{68}$-1-L-lysine, 6-glycine)-bradykinin] where N-terminal bradykinin arginine is substituted by L-lysine, and serine in position 6 of bradykinin is substituted by glycine, the cycle is closed with peptide bond formed by arginine carbonyl group and ε-amino group of lysine of the formula

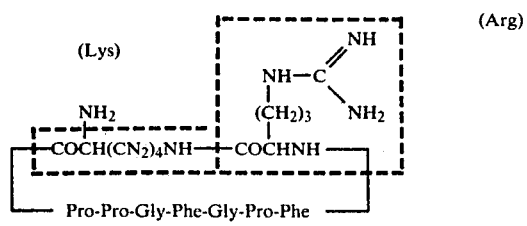

where Lys -L-lysine residue, Pro -L-proline residue, Gly -glycine residue, Phe -L-phenylalanine residue, Arg - L-arginine residue.

* * * * *